(12) United States Patent
Birdsall (10) Patent No.: US 7,740,655 B2
(45) Date of Patent: Jun. 22, 2010

(54) REINFORCED SURGICAL CONDUIT FOR IMPLANTATION OF A STENTED VALVE THEREIN

(75) Inventor: Matthew J. Birdsall, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 807 days.

(21) Appl. No.: 11/278,932

(22) Filed: Apr. 6, 2006

(65) Prior Publication Data
US 2007/0239266 A1    Oct. 11, 2007

(51) Int. Cl.
*A61F 2/06*    (2006.01)
(52) U.S. Cl. .................................. 623/1.24; 623/2.11
(58) Field of Classification Search ....... 623/1.24–1.54, 623/2.1–2.19
See application file for complete search history.

(56) References Cited

U.S. PATENT DOCUMENTS

| | | | |
|---|---|---|---|
| 3,334,629 A | 8/1967 | Cohn |
| 3,540,431 A | 11/1970 | Mobin-Uddin |
| 3,628,535 A | 12/1971 | Ostrowsky et al. |
| 3,642,004 A | 2/1972 | Osthagen et al. |
| 3,657,744 A | 4/1972 | Esek |
| 3,671,979 A | 6/1972 | Moulopoulos |
| 3,795,246 A | 3/1974 | Sturgeon |
| 3,839,741 A | 10/1974 | Haller |
| 3,868,956 A | 3/1975 | Alfidi et al. |
| 3,874,388 A | 4/1975 | King et al. |
| 4,056,854 A | 11/1977 | Boretos et al. |
| 4,106,129 A | 8/1978 | Carpentier et al. |
| 4,233,690 A | 11/1980 | Akins |
| 4,291,420 A | 9/1981 | Reul |
| 4,425,908 A | 1/1984 | Simon |
| 4,501,030 A | 2/1985 | Lane |
| 4,580,568 A | 4/1986 | Gianturco |

(Continued)

FOREIGN PATENT DOCUMENTS

EP    1057459    2/2000

(Continued)

OTHER PUBLICATIONS

P. Bonhoeffer, MD, et al., "Transcatheter Implantation of a Bovine Valve in a Pulmonary Position—A Lamb Study," pp. 8-3-816; Aug. 2000.

(Continued)

*Primary Examiner*—Suzette J Gherbi (57) ABSTRACT

A pulmonary valve replacement system having a vascular conduit and a prosthetic valve device including a valve operably connected to a support structure. The prosthetic valve device is positioned within the vascular conduit. A conduit support includes a substantially circular cross-section. The conduit support is positioned adjacent to and reinforces the vascular conduit. In one embodiment, the pulmonary valve replacement system includes a catheter and an inflatable member operably attached to the catheter. The prosthetic valve device is disposed on the inflatable member. The invention provides a method for replacing a pulmonary valve including providing a vascular conduit positioned at a treatment site. The vascular conduit includes a conduit support positioned adjacent the vascular conduit. A prosthetic valve device is deployed within the vascular conduit via catheter. The prosthetic valve device includes a valve operably connected to a support structure. The vascular conduit is supported with the conduit support.

11 Claims, 7 Drawing Sheets

U.S. PATENT DOCUMENTS

| | | | |
|---|---|---|---|
| 4,610,688 A | 9/1986 | Silvestrini et al. |
| 4,647,283 A | 3/1987 | Carpentier et al. |
| 4,648,881 A | 3/1987 | Carpentier et al. |
| 4,655,771 A | 4/1987 | Wallsten |
| 4,662,885 A | 5/1987 | DiPisa, Jr. |
| 4,665,906 A | 5/1987 | Jervis |
| 4,710,192 A | 12/1987 | Liotta et al. |
| 4,733,665 A | 3/1988 | Palmaz |
| 4,819,751 A | 4/1989 | Shimada et al. |
| 4,834,755 A | 5/1989 | Silvestrini et al. |
| 4,856,516 A | 8/1989 | Hillstead |
| 4,872,874 A | 10/1989 | Taheri |
| 4,909,252 A | 3/1990 | Goldberger |
| 4,917,102 A | 4/1990 | Miller et al. |
| 4,954,126 A | 9/1990 | Wallsten |
| 4,994,077 A | 2/1991 | Dobben |
| 5,002,559 A | 3/1991 | Tower |
| 5,156,621 A | 10/1992 | Navia et al. |
| 5,161,547 A | 11/1992 | Tower |
| 5,163,953 A | 11/1992 | Vince |
| 5,197,979 A | 3/1993 | Quintero et al. |
| 5,217,483 A | 6/1993 | Tower |
| 5,332,402 A | 7/1994 | Teitelbaum et al. |
| 5,336,258 A | 8/1994 | Quintero et al. |
| 5,350,398 A | 9/1994 | Pavcnik et al. |
| 5,370,685 A | 12/1994 | Stevens |
| 5,389,106 A | 2/1995 | Tower |
| 5,397,351 A | 3/1995 | Pavcnik et al. |
| 5,411,552 A | 5/1995 | Andersen et al. |
| 5,431,676 A | 7/1995 | Dubrul et al. |
| 5,500,014 A * | 3/1996 | Quijano et al. | 623/1.24 |
| 5,507,767 A | 4/1996 | Maeda et al. |
| 5,545,211 A | 8/1996 | An et al. |
| 5,554,185 A | 9/1996 | Block et al. |
| 5,575,818 A | 11/1996 | Pinchuk |
| 5,645,559 A | 7/1997 | Hachtman et al. |
| 5,667,523 A | 9/1997 | Bynon et al. |
| 5,674,277 A | 10/1997 | Freitag |
| 5,695,498 A | 12/1997 | Tower |
| 5,713,953 A | 2/1998 | Vallana et al. |
| 5,800,456 A | 9/1998 | Maeda et al. |
| 5,817,126 A | 10/1998 | Imran |
| 5,824,043 A | 10/1998 | Cottone, Jr. |
| 5,824,053 A | 10/1998 | Khosravi et al. |
| 5,824,056 A | 10/1998 | Rosenberg |
| 5,824,064 A | 10/1998 | Taheri |
| 5,840,081 A | 11/1998 | Andersen et al. |
| 5,855,597 A | 1/1999 | Jayaraman |
| 5,855,601 A | 1/1999 | Bessler et al. |
| 5,860,966 A | 1/1999 | Tower |
| 5,861,028 A | 1/1999 | Angell |
| 5,868,783 A | 2/1999 | Tower |
| 5,876,448 A | 3/1999 | Thompson et al. |
| 5,888,201 A | 3/1999 | Stinson et al. |
| 5,891,191 A | 4/1999 | Stinson |
| 5,907,893 A | 6/1999 | Zadno-Azizi et al. |
| 5,925,063 A | 7/1999 | Khosravi |
| 5,944,738 A | 8/1999 | Amplatz et al. |
| 5,954,766 A * | 9/1999 | Zadno-Azizi et al. | 623/1.24 |
| 5,957,949 A | 9/1999 | Leonhardt et al. |
| 5,984,957 A | 11/1999 | Laptewicz, Jr. et al. |
| 6,001,126 A | 12/1999 | Nguyen-Thien-Nhon |
| 6,027,525 A | 2/2000 | Suh et al. |
| 6,042,598 A | 3/2000 | Tsugita et al. |
| 6,051,014 A | 4/2000 | Jang |
| 6,123,723 A | 9/2000 | Konya et al. |
| 6,146,366 A | 11/2000 | Schachar |
| 6,162,245 A | 12/2000 | Jayaraman |
| 6,168,614 B1 | 1/2001 | Andersen et al. |
| 6,200,336 B1 | 3/2001 | Pavcnik et al. |
| 6,221,006 B1 | 4/2001 | Dubrul et al. |
| 6,221,091 B1 | 4/2001 | Khosravi |
| 6,241,757 B1 | 6/2001 | An et al. |
| 6,245,102 B1 * | 6/2001 | Jayaraman | 623/1.15 |
| 6,254,436 B1 | 7/2001 | Nitta et al. |
| 6,258,114 B1 | 7/2001 | Konya et al. |
| 6,258,115 B1 | 7/2001 | Dubrul et al. |
| 6,258,120 B1 | 7/2001 | McKenzie et al. |
| 6,277,555 B1 | 8/2001 | Duran et al. |
| 6,299,637 B1 * | 10/2001 | Shaolian et al. | 623/1.24 |
| 6,309,417 B1 | 10/2001 | Spence et al. |
| 6,327,772 B1 | 12/2001 | Zadno-Aziz et al. |
| 6,338,735 B1 | 1/2002 | Stevens |
| 6,342,070 B1 | 1/2002 | Nguyen-Thien-Nhon |
| 6,348,063 B1 | 2/2002 | Yassour et al. |
| 6,350,282 B1 | 2/2002 | Eberhardt |
| 6,352,708 B1 | 3/2002 | Duran et al. |
| 6,364,905 B1 | 4/2002 | Simpson et al. |
| 6,371,970 B1 | 4/2002 | Khosravi et al. |
| 6,371,983 B1 | 4/2002 | Lane |
| 6,379,383 B1 | 4/2002 | Palmaz et al. |
| 6,398,807 B1 | 6/2002 | Chouinard et al. |
| 6,409,750 B1 | 6/2002 | Hyodoh et al. |
| 6,425,916 B1 | 7/2002 | Garrison et al. |
| 6,440,164 B1 * | 8/2002 | DiMatteo et al. | 623/1.24 |
| 6,458,153 B1 | 10/2002 | Bailey et al. |
| 6,468,303 B1 | 10/2002 | Amplatz et al. |
| 6,475,239 B1 | 11/2002 | Campbell |
| 6,482,228 B1 | 11/2002 | Norred |
| 6,494,909 B2 | 12/2002 | Greenhalgh |
| 6,503,272 B2 | 1/2003 | Duerig et al. |
| 6,508,833 B2 | 1/2003 | Pavcnik et al. |
| 6,509,930 B1 | 1/2003 | Hirano et al. |
| 6,527,800 B1 | 3/2003 | McGuckin, Jr. et al. |
| 6,530,949 B2 | 3/2003 | Konya et al. |
| 6,530,952 B2 | 3/2003 | Vesely |
| 6,558,417 B2 | 5/2003 | Peredo |
| 6,562,058 B2 | 5/2003 | Seguin et al. |
| 6,569,196 B1 | 5/2003 | Vesely |
| 6,592,546 B1 | 7/2003 | Barbut et al. |
| 6,622,604 B1 | 9/2003 | Chouinard et al. |
| 6,632,243 B1 | 10/2003 | Zadno-Azizi et al. |
| 6,635,068 B1 | 10/2003 | Dubrul et al. |
| 6,652,571 B1 | 11/2003 | White et al. |
| 6,652,578 B2 | 11/2003 | Bailey et al. |
| 6,652,582 B1 * | 11/2003 | Stinson | 623/1.39 |
| 6,663,663 B2 | 12/2003 | Kim et al. |
| 6,669,724 B2 | 12/2003 | Park et al. |
| 6,673,089 B1 | 1/2004 | Yassour et al. |
| 6,673,109 B2 | 1/2004 | Cox |
| 6,682,558 B2 | 1/2004 | Tu et al. |
| 6,682,559 B2 | 1/2004 | Myers et al. |
| 6,685,739 B2 | 2/2004 | DiMatteo et al. |
| 6,689,144 B2 | 2/2004 | Gerberding |
| 6,689,164 B1 | 2/2004 | Seguin |
| 6,692,512 B2 | 2/2004 | Jang |
| 6,702,851 B1 | 3/2004 | Chinn et al. |
| 6,719,789 B2 | 4/2004 | Cox |
| 6,730,118 B2 | 5/2004 | Spenser et al. |
| 6,730,377 B2 | 5/2004 | Wang |
| 6,733,525 B2 | 5/2004 | Yang et al. |
| 6,736,846 B2 | 5/2004 | Cox |
| 6,752,828 B2 | 6/2004 | Thornton |
| 6,758,855 B2 | 7/2004 | Fulton, III et al. |
| 6,769,434 B2 | 8/2004 | Liddicoat et al. |
| 6,887,266 B2 | 5/2005 | Williams et al. |
| 6,890,330 B2 | 5/2005 | Streeter et al. |
| 6,896,690 B1 | 5/2005 | Lambrecht et al. |
| 6,929,653 B2 | 8/2005 | Streeter |
| 2001/0007956 A1 | 7/2001 | Letac et al. |
| 2001/0025196 A1 | 9/2001 | Chinn et al. |
| 2001/0032013 A1 | 10/2001 | Marton |
| 2001/0039450 A1 | 11/2001 | Pavcnik et al. |
| 2001/0041928 A1 | 11/2001 | Pavcnik et al. |

| | | |
|---|---|---|
| 2002/0032480 A1 | 3/2002 | Spence et al. |
| 2002/0032481 A1 | 3/2002 | Gabbay |
| 2002/0052651 A1 | 5/2002 | Myers et al. |
| 2002/0058995 A1 | 5/2002 | Stevens |
| 2002/0077696 A1 | 6/2002 | Zadno-Azizi et al. |
| 2002/0095209 A1 | 7/2002 | Zadno-Azizi et al. |
| 2002/0111674 A1 | 8/2002 | Chouinard et al. |
| 2002/0151970 A1 | 10/2002 | Garrison et al. |
| 2002/0161392 A1 | 10/2002 | Dubrul |
| 2002/0161394 A1 | 10/2002 | Macoviak et al. |
| 2002/0193871 A1 | 12/2002 | Beyersdorf et al. |
| 2003/0014104 A1 | 1/2003 | Cribier |
| 2003/0023303 A1 | 1/2003 | Palmaz et al. |
| 2003/0028247 A1 | 2/2003 | Cali |
| 2003/0036791 A1 | 2/2003 | Philipp et al. |
| 2003/0040771 A1 | 2/2003 | Hyodoh et al. |
| 2003/0040772 A1 | 2/2003 | Hyodoh et al. |
| 2003/0055495 A1 | 3/2003 | Pease et al. |
| 2003/0069635 A1 | 4/2003 | Cartledge et al. |
| 2003/0109924 A1 | 6/2003 | Cribier |
| 2003/0125795 A1 | 7/2003 | Pavcnik et al. |
| 2003/0125805 A1 | 7/2003 | Johnson et al. |
| 2003/0130729 A1 | 7/2003 | Paniagua et al. |
| 2003/0149475 A1 | 8/2003 | Hyodoh et al. |
| 2003/0149476 A1 | 8/2003 | Damm et al. |
| 2003/0149478 A1 | 8/2003 | Figulla et al. |
| 2003/0153974 A1 | 8/2003 | Spenser et al. |
| 2003/0181850 A1 | 9/2003 | Diamond et al. |
| 2003/0199913 A1 | 10/2003 | Dubrul et al. |
| 2003/0199963 A1 | 10/2003 | Tower et al. |
| 2003/0199972 A1 | 10/2003 | Zadno-Azizi et al. |
| 2003/0212452 A1 | 11/2003 | Zadno-Azizi et al. |
| 2003/0212454 A1 | 11/2003 | Scott et al. |
| 2004/0034411 A1 | 2/2004 | Quijano et al. |
| 2004/0039436 A1 | 2/2004 | Spenser et al. |
| 2004/0049224 A1 | 3/2004 | Buehlmann et al. |
| 2004/0049262 A1 | 3/2004 | Obermiller et al. |
| 2004/0049266 A1 | 3/2004 | Anduiza et al. |
| 2004/0082904 A1 | 4/2004 | Houde et al. |
| 2004/0088045 A1 | 5/2004 | Cox |
| 2004/0098112 A1 | 5/2004 | DiMatteo et al. |
| 2004/0106984 A1* | 6/2004 | Stinson ............... 623/1.15 |
| 2004/0111096 A1 | 6/2004 | Tu et al. |
| 2004/0116951 A1 | 6/2004 | Rosengart |
| 2004/0117004 A1 | 6/2004 | Osborne et al. |
| 2004/0122468 A1 | 6/2004 | Yodfat et al. |
| 2004/0127979 A1 | 7/2004 | Wilson |
| 2004/0138742 A1 | 7/2004 | Myers et al. |
| 2004/0138743 A1 | 7/2004 | Myers et al. |
| 2004/0186563 A1 | 9/2004 | Lobbi |
| 2004/0215339 A1 | 10/2004 | Drasler et al. |
| 2005/0085841 A1 | 4/2005 | Eversull et al. |
| 2005/0085842 A1 | 4/2005 | Eversull et al. |
| 2005/0085843 A1 | 4/2005 | Opolski et al. |
| 2005/0085890 A1 | 4/2005 | Rasmussen et al. |
| 2005/0096692 A1 | 5/2005 | Linder et al. |
| 2005/0096734 A1 | 5/2005 | Majercak et al. |
| 2005/0096735 A1 | 5/2005 | Hojeibane et al. |
| 2005/0096738 A1 | 5/2005 | Cali et al. |
| 2005/0209065 A1 | 9/2005 | Schlosser |
| 2005/0251251 A1 | 11/2005 | Cribier |
| 2006/0052867 A1 | 3/2006 | Revuelta et al. |
| 2006/0247762 A1* | 11/2006 | Acosta et al. ............. 623/1.24 |
| 2007/0244546 A1* | 10/2007 | Francis ............... 623/1.26 |
| 2008/0183280 A1* | 7/2008 | Agnew et al. ............. 623/1.24 |

| | | |
|---|---|---|
| 2009/0254174 A1* | 10/2009 | Case et al. ............. 623/1.17 |

FOREIGN PATENT DOCUMENTS

| | | |
|---|---|---|
| EP | 0937439 B1 | 9/2003 |
| EP | 1340473 | 9/2003 |
| EP | 1356793 | 10/2003 |
| EP | 0810913 | 6/2004 |
| EP | 1229864 B1 | 4/2005 |
| FR | 2 826 863 | 1/2003 |
| WO | WO 93/15693 | 8/1993 |
| WO | WO 95/04556 | 2/1995 |
| WO | WO 95/29640 | 11/1995 |
| WO | WO 96/14032 | 5/1996 |
| WO | WO 98/36790 | 8/1998 |
| WO | WO 00/09059 | 2/2000 |
| WO | WO 00/44308 | 8/2000 |
| WO | WO 00/44313 | 8/2000 |
| WO | WO 00/67661 | 11/2000 |
| WO | WO 01/05331 | 1/2001 |
| WO | WO 01/35870 | 5/2001 |
| WO | WO 01/64137 | 9/2001 |
| WO | WO 02/36048 | 5/2002 |
| WO | WO 02/100297 | 12/2002 |
| WO | WO 03/003943 | 1/2003 |
| WO | WO 03/003949 | 1/2003 |
| WO | WO 03/011195 | 2/2003 |
| WO | WO 03/015851 | 2/2003 |
| WO | WO 2004/019811 | 3/2004 |
| WO | WO 2004/023980 | 3/2004 |
| WO | WO 2004/041126 | 5/2004 |
| WO | WO 2004/047681 | 6/2004 |
| WO | WO 2005/013860 | 2/2005 |

OTHER PUBLICATIONS

P. Bonhoeffer, MD et al., "Percutaneous Replacement of Pulmonary Valve in a Right-Ventricle to Pulmonary-Artery Prosthetic Conduit with Valve Dysfunction," pp. 1403-1405; Oct. 2000.

Y. Boudjemline, MD, et al., "Steps Towards Percutaneous Aortic Valve Replacement," pp. 775-778; Feb. 2002.

P. Bonhoeffer, MD, et al., "Percutaneous Insertion of the Pulmonary Valve," Journal of the American College of Cardiology, vol. 39, No. 10, pp. 1664-1669; Feb. 2002.

A Cribier, MD, et al., "Percutaneous Transcatheter Implantation of an Aortic Valve Prosthesis for Calcific Aortic Stenosis—First Human Description," pp. 3006-3008; Dec. 2002.

A. Cribier, MD, et al.; "Early Experience with Percutaneous Transcatheter Implantation of Heart Valve Prosthesis for the Treatment of End-Stage Inoperable Patients with Calcific Aortic Stenosis," Journal of the American College of Cardiology, vol. 43, No. 4, pp. 698-703; Nov. 2003.

Y. Boudjemline, MD. et al., "Percutaneous Pulmonary Valve Replacement in a Large Right Ventricular Outflow Tract," Journal of the American College of Cardiology, vol. 43, No. 6; pp. 1082-1087; Mar. 2004.

Andersen, H.R. et al, "Tran luminal implantation of artificial heart valves. Description of a new expandable aortic valve and initial results with implantation by catheter technique in closed chest pigs." Euro. Heart J. (1992) 13:704-708.

Bonhoeffer, "Percutaneous insertion of the pulmonary valve," Journal of American College of Cardiology Foundation, (2002) 39(0):1664-1669.

Iliopoulos, et al., "Repeat replacement of aortic valve bioprosthesis," Ann. Thorac Surg. (1995), 59:1217-1219.

* cited by examiner

REINFORCED SURGICAL CONDUIT FOR IMPLANTATION OF A STENTED VALVE THEREIN

TECHNICAL FIELD OF THE INVENTION

This invention relates generally to medical devices for treating cardiac valve abnormalities, and particularly to a pulmonary valve replacement system and method of operating the same.

BACKGROUND OF THE INVENTION

Heart valves, such as the mitral, tricuspid, aortic and pulmonary valves, are sometimes damaged by disease or by aging, resulting in problems with the proper functioning of the valve. Heart valve problems generally take one of two forms: stenosis, in which a valve does not open completely or the opening is too small, resulting in restricted blood flow; or insufficiency, in which blood leaks backward across a valve when it should be closed.

The pulmonary valve regulates blood flow between the right ventricle and the pulmonary artery, controlling blood flow between the heart and the lungs. Pulmonary valve stenosis is frequently due to a narrowing of the pulmonary valve or the pulmonary artery distal to the valve. This narrowing causes the right side of the heart to exert more pressure to provide sufficient flow to the lungs. Over time, the right ventricle enlarges, which leads to congestive heart failure (CHF). In severe cases, the CHF results in clinical symptoms including shortness of breath, fatigue, chest pain, fainting, heart murmur, and in babies, poor weight gain. Pulmonary valve stenosis most commonly results from a congenital defect, and is present at birth, but is also associated with rheumatic fever, endocarditis, and other conditions that cause damage to or scarring of the pulmonary valve. Valve replacement may be required in severe cases to restore cardiac function.

Previously, valve repair or replacement required open-heart surgery with its attendant risks, expense, and extended recovery time. Open-heart surgery also requires cardiopulmonary bypass with risk of thrombosis, stroke, and infarction. More recently, flexible valve prostheses and various delivery devices have been developed so that replacement valves can be implanted transvenously using minimally invasive techniques. As a consequence, replacement of the pulmonary valve has become a treatment option for pulmonary valve stenosis.

The most severe consequences of pulmonary valve stenosis occur in infants and young children when the condition results from a congenital defect. Frequently, the pulmonary valve must be replaced with a prosthetic valve when the child is young, usually less than five years of age. However, as the child grows, the valve can become too small to accommodate the blood flow to the lungs that is needed to meet the increasing energy demands of the growing child, and it may then need to be replaced with a larger valve. Alternatively, in a patient of any age, the implanted valve may fail to function properly due to calcium buildup and have to be replaced. In either case, repeated surgical or transvenous procedures are required.

To address the need for pulmonary valve replacement, various implantable pulmonary valve prostheses, delivery devices and surgical techniques have been developed and are presently in use. One such prosthesis is a bioprosthetic, valved conduit comprising a glutaraldehyde treated bovine jugular vein containing a natural, trileaflet venous valve, and sinus. A similar device is composed of a porcine aortic valve sutured into the center of a woven fabric conduit. A common conduit used in valve replacement procedures is a homograft, which is a vessel harvested from a cadaver. Valve replacement using either of these devices requires thoracotomy and cardiopulmonary bypass.

When the valve in the prostheses must be replaced, for the reasons described above or other reasons, an additional surgery is required. Because many patients undergo their first procedure at a very young age, they often undergo numerous procedures by the time they reach adulthood. These surgical replacement procedures are physically and emotionally taxing, and a number of patients choose to forgo further procedures after they are old enough to make their own medical decisions.

Recently, implantable stented valves have been developed that can be delivered transvenously using a catheter-based delivery system. These stented valves comprise a collapsible valve attached to the interior of a tubular frame or stent. The valve can be any of the valve prostheses described above, or it can be any other suitable valve. In the case of valves in harvested vessels, the vessel can be of sufficient length to extend beyond both sides of the valve such that it extends to both ends of the valve support stent.

The stented valves can also comprise a tubular portion or "stent graft" that can be attached to the interior or exterior of the stent to provide a generally tubular internal passage for the flow of blood when the leaflets are open. The graft can be separate from the valve and it can be made from any suitable biocompatible material including, but not limited to, fabric, a homograft, porcine vessels, bovine vessels, and equine vessels.

The stent portion of the device can be reduced in diameter, mounted on a catheter, and advanced through the circulatory system of the patient. The stent portion can be either self-expanding or balloon expandable. In either case, the stented valve can be positioned at the delivery site, where the stent portion is expanded against the wall of a previously implanted prostheses or a native vessel to hold the valve firmly in place.

One embodiment of a stented valve is disclosed in U.S. Pat. No. 5,957,949 titled "Percutaneous Placement Valve Stent" to Leonhardt, et al, the contents of which are incorporated herein by reference.

Although the use of stented valves can obviate the need for open-heart surgery during installation, the stents are difficult to remove if replacement of the valve becomes necessary due to either the growth of the patient or calcification of the leaflets. Because the stent portion of the implantable valve is in tight contact with the vessel wall, it induces fibrosis in the surrounding vascular tissue, and is frequently infiltrated with tissue. To remove the stented valve, the stent portion must be cut from the vessel wall. This difficult procedure incurs a risk that the vessel wall will be punctured, and usually must be performed in an open surgical procedure.

In some cases, over time, the implanted pulmonary valve prostheses may deform and not be symmetrical. While this asymmetry is not necessarily damaging to the patient it is, however, problematic for delivering a stented valve therein. Accordingly, it would be desirable to provide an implantable pulmonary valve prosthesis that resists deformation and remains substantially symmetrical.

As such; it would be desirable to provide pulmonary valve prostheses that would overcome the aforementioned and other disadvantages.

SUMMARY OF THE INVENTION

It is an object of the present invention to provide a vascular valve replacement system having at least a conduit and a replacement valve device disposed in the conduit.

The system and the prosthetic valve will be described herein as being used for replacing a pulmonary valve. The pulmonary valve is also known to those having skill in the art as the "pulmonic valve" and as used herein, those terms shall be considered to mean the same thing.

Thus, a first aspect according to the present invention provides a pulmonary valve replacement system having a vascular conduit and a prosthetic valve device including a valve operably connected to a support structure. The prosthetic valve device is positioned within the vascular conduit. A conduit support includes a substantially circular cross-section. The conduit support is positioned adjacent to and reinforces the vascular conduit.

A second aspect according to the present invention provides a pulmonary valve replacement system having a catheter, an inflatable member operably attached to the catheter, and a vascular conduit. A prosthetic valve device including a valve is operably connected to a support structure. The prosthetic valve device is positioned within the vascular conduit and disposed on the inflatable member. A conduit support includes a substantially circular cross-section. The conduit support is positioned adjacent to and reinforces the vascular conduit.

A third aspect according to the present invention provides a method for replacing a pulmonary valve. The method includes providing a vascular conduit positioned at a treatment site, the vascular conduit includes a conduit support positioned adjacent the vascular conduit. A prosthetic valve device is deployed within the vascular conduit via catheter. The prosthetic valve device includes a valve operably connected to a support structure. The vascular conduit is supported with the conduit support.

The present invention is illustrated by the accompanying drawings of various embodiments and the detailed description given below. The drawings should not be taken to limit the invention to the specific embodiments, but are for explanation and understanding. The detailed description and drawings are merely illustrative of the invention rather than limiting, the scope of the invention being defined by the appended claims and equivalents thereof. The drawings are not to scale. The foregoing aspects and other attendant advantages of the present invention will become more readily appreciated by the detailed description taken in conjunction with the accompanying drawings.

DESCRIPTION OF THE PRESENTLY PREFERRED EMBODIMENTS

The invention will now be described by reference to the drawings wherein like numbers refer to like structures.

Figure 1:
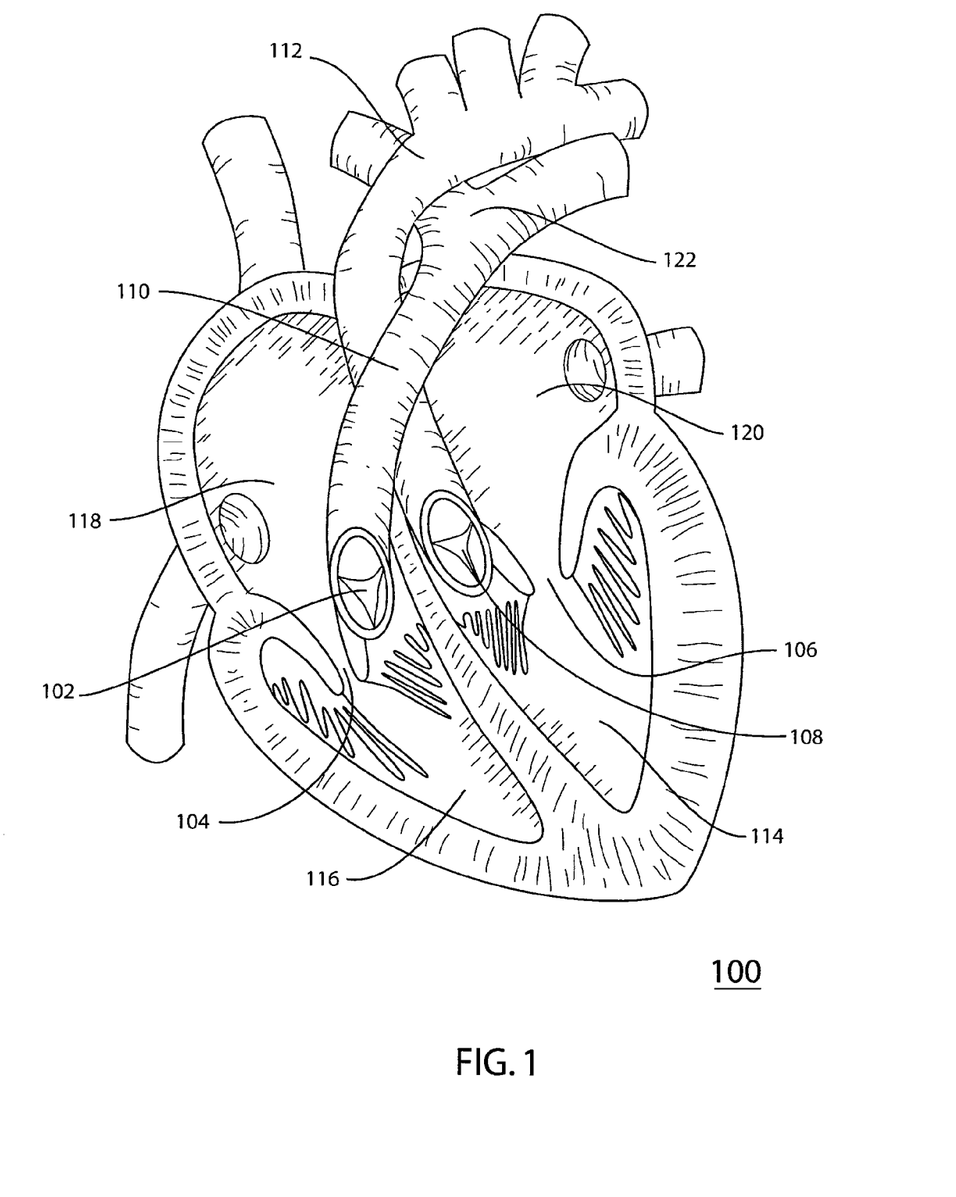
FIG. 1 is a schematic interior view of a human heart showing the functioning of the four heart valves.

Referring to the drawings, FIG. 1 is a schematic representation of the interior of human heart 100. Human heart 100 includes four valves that work in synchrony to control the flow of blood through the heart. Tricuspid valve 104, situated between right atrium 118 and right ventricle 116, and mitral valve 106, between left atrium 120 and left ventricle 114 facilitate filling of ventricles 116 and 114 on the right and left sides, respectively, of heart 100. Aortic valve 108 is situated at the junction between aorta 112 and left ventricle 114 and facilitates blood flow from heart 100, through aorta 112 to the peripheral circulation.

Pulmonary valve 102 is situated at the junction of right ventricle 116 and pulmonary artery 110 and facilitates blood flow from heart 100 through the pulmonary artery 110 to the lungs for oxygenation. The four valves work by opening and closing in harmony with each other. During diastole, tricuspid valve 104 and mitral valve 106 open and allow blood flow into ventricles 114 and 116, and the pulmonic valve and aortic valve are closed. During systole, shown in FIG. 1, aortic valve 108 and pulmonary valve 102 open and allow blood flow from left ventricle 114, and right ventricle 116 into aorta 112 and pulmonary 110, respectively.

The right ventricular outflow tract is the segment of pulmonary artery 110 that includes pulmonary valve 102 and extends to branch point 122, where pulmonary artery 110 forms left and right branches that carry blood to the left and right lungs respectively. A defective pulmonary valve or other abnormalities of the pulmonary artery that impede blood flow from the heart to the lungs sometimes require surgical repair or replacement of the right ventricular outflow tract with prosthetic conduit 202, as shown in FIG. 2A-C.

Such conduits comprise tubular structures of biocompatible materials, with a hemocompatible interior surface. Examples of appropriate biocompatible materials include polytetrafluoroethylene (PTFE), woven polyester fibers such as Dacron® fibers (E.I. Du Pont De Nemours & Co., Inc.), and bovine vein cross linked with glutaraldehyde. One common conduit is a homograft, which is a vessel harvested from a cadaver and treated for implantation into a recipient's body. These conduits may contain a valve at a fixed position within the interior lumen of the conduit that functions as a replacement pulmonary valve. One such conduit 202 comprises a bovine jugular vein with a trileaflet venous valve preserved in buffered glutaraldehyde.

Other valves are made of xeno-pericardial tissue and are attached to the wall of the lumen of the conduit. Still other valves may be made at least partially from some synthetic material. The conduits may also include materials having a high X-ray attenuation coefficient (radiopaque materials) that are woven into or otherwise attached to the conduit, so that it can be easily located and identified.

Figure 2A:
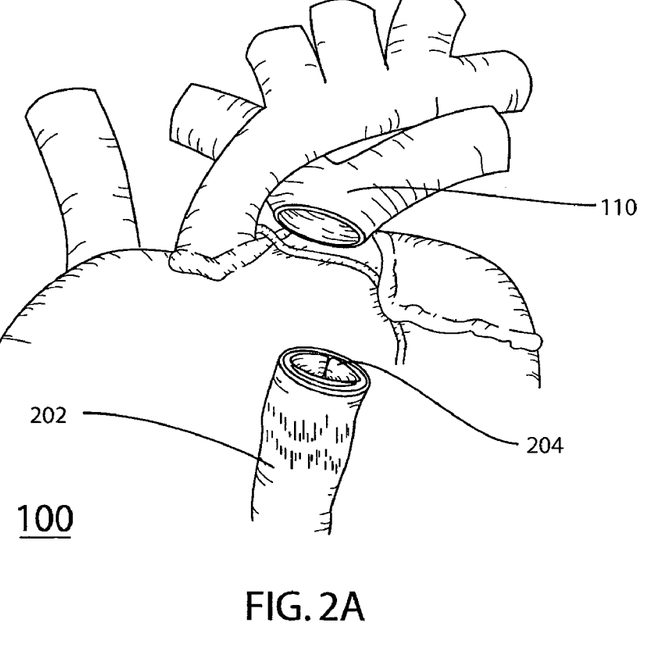
FIG. 2A is a schematic view showing the placement of a pulmonary conduit, as is known in the prior art.
Figure 2B:
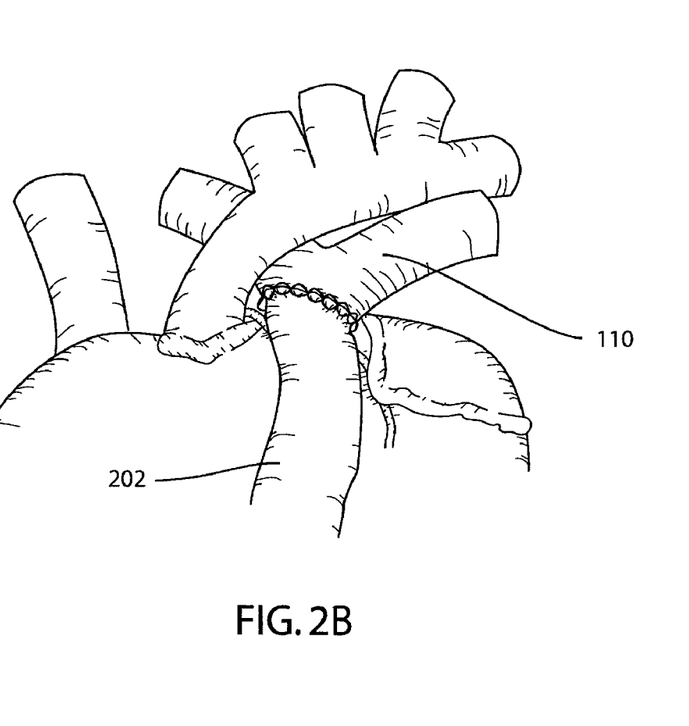
FIG. 2B is a schematic view showing attachment of a pulmonary conduit to the pulmonary artery, as is known in the prior art.
Figure 2C:
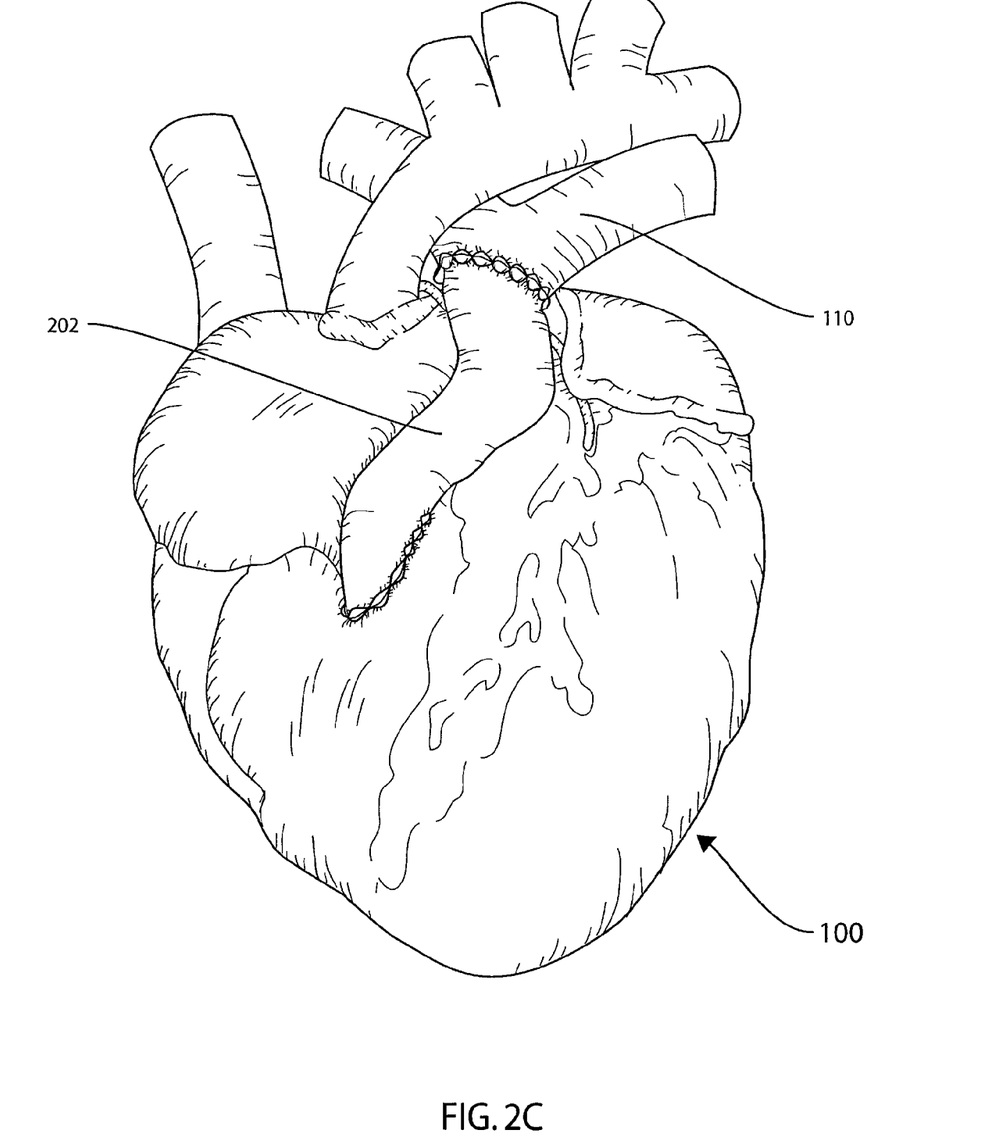
FIG. 2C is a schematic view showing attachment of a pulmonary conduit to the heart, as is known in the prior art.

As shown in FIGS. 2A and 2B, conduit 202, which houses valve 204 within its inner lumen, is installed within a patient by sewing the distal end of conduit 202 to pulmonary artery 110, and, as shown in FIG. 2C, attaching the proximal end of conduit 202 to heart 100 so that the lumen of conduit 202 connects to right ventricle 116.

Over time, implanted prosthetic conduits and valves are frequently subject to calcification, causing the affected conduit or valve to lose flexibility, become misshapen, and lose the ability to function effectively. Additional problems are encountered when prosthetic valves are implanted in young children. As the child grows, the valve will ultimately be too small to handle the increased volume of blood flowing from the heart to the lungs. In either case, the valve needs to be replaced.

One method of valve replacement is a catheter delivered stented valve. When using this method, a delivery catheter carrying a stented valve can be passed through the venous system and into a patient's right ventricle. This may be accomplished by inserting the delivery catheter into either the jugular vein or the subclavian vein and passing it through superior vena cava into right atrium. The catheter is then passed through the tricuspid valve, into right ventricle, and out of the ventricle into the conduit. Alternatively, the catheter may be inserted into the femoral vein and passed through the common iliac vein and the inferior vena cava into the right atrium, then through the tricuspid valve, into the right ventricle and out into the conduit. The catheters used for the procedures described herein may include radiopaque markers as are known in the art, and the procedure may be visualized using fluoroscopy, echocardiography, ultrasound, or other suitable means of visualization. In some cases, over time, the implanted pulmonary valve prostheses may deform and not be symmetrical. While this asymmetry is not necessarily damaging to the patient it is, however, problematic for delivering and seating a stented valve therein.

Figure 3:
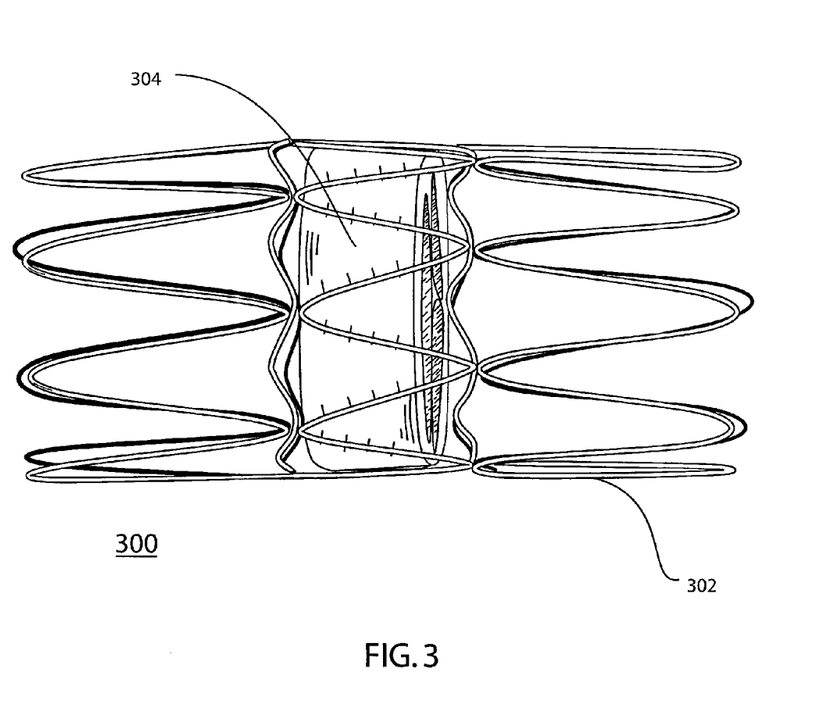
FIG. 3 is a cross-sectional side view of a prosthetic valve device including a valve, in accordance with the present invention.

FIG. 3 is a cross-sectional side view of prosthetic valve device 300 including a valve 304, having a support structure 302 operably connected to the valve 304 to assist in maintaining the symmetry of the conduit so that delivery of a stented valve may be more easily accomplished. The valve 304, includes three leaflets of a flexible material and it is situated within the lumen of support structure 302

Figure 4:
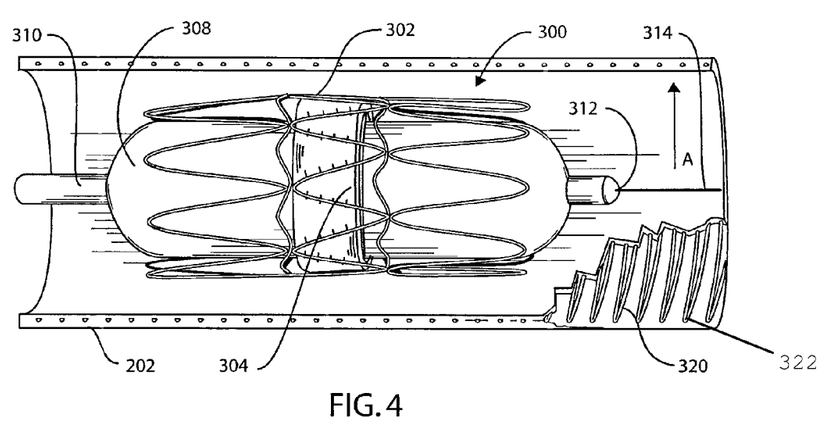
FIG. 4 is a schematic view of a prosthetic valve device situated in a vascular conduit, in accordance with the present invention.

In one embodiment of the invention, shown in FIG. 4, support structure 302 is an expandable stent made of a flexible, biocompatible material that has "shape memory", such as nitinol. Support structure 302 retains the prosthetic valve device 300 within the vascular conduit 202. Prosthetic valve device 300 is compressed and disposed on an inflatable member 308, which is operably attached to a catheter 310. Catheter 310 delivers prosthetic valve device 300 endovascularly to a treatment site within the vascular conduit 202. Prosthetic valve device 300 is positioned within the vascular conduit 202 and then expanded with an inflatable member 308.

In one embodiment, catheter 310 is an elongated tubular member manufactured from one or more polymeric materials, sometimes in combination with metallic reinforcement. In some applications (such as smaller, more tortuous arteries), it is desirable to construct the catheter from very flexible materials to facilitate advancement into intricate access locations. Numerous over-the-wire, rapid-exchange, and other catheter designs are known and may be adapted for use with the present invention. Catheter 310 can be secured at its proximal end to a suitable Luer fitting, and includes a distal rounded end 312 to reduce harmful contact with a vessel wall. Catheter 310 is manufactured from a material such as a thermoplastic elastomer, urethane, polymer, polypropylene, plastic, ethelene chlorotrifluoroethylene (ECTFE), polytetrafluoroethylene (PTFE), fluorinated ethylene propylene copolymer (FEP), nylon, Pebax® resin, Vestamid® nylon, Tecoflex® resin, Halar® resin, Hyflon® resin, Pellathane® resin, combinations thereof, and the like. Catheter 310 includes an aperture formed at the distal rounded end 312 allowing advancement over a guidewire 314.

In one embodiment, inflatable member 308 is any variety of balloon or other device capable of expanding the prosthetic valve device 300. Inflatable member 308 is manufactured from any suitable material such as polyethylene, polyethylene terephthalate (PET), nylon, or the like. Those skilled in the art will recognize that the prosthetic valve device 300 may be expanded using a variety of means and that the present invention is not limited to balloon expansion.

Vascular conduit 202 is designed to be a long term implant and frequently can become calcified or subject to fibrotic ingrowth of tissue, either of which sometimes causes the vascular conduit 202 to become misshapen, so that its cross section is no longer round and symmetrical. Consequently, prosthetic valve device 300 would not fit well within a misshapen vascular conduit 202, and may be ineffective either because of blood flowing around the outside of valve 304, or because valve 304 cannot be aligned perpendicularly to the flow of blood through vascular conduit 202.

To reduce or eliminate the chance of having a vascular conduit become misshapen after implantation, a conduit support 320 having a substantially circular cross-section is positioned adjacent to or within the vascular conduit 202. Conduit support 320 provides reinforcement along the length of the vascular conduit 202 in a radial direction A, which is substantially perpendicular to the direction of blood flow through the vascular conduit 202.

The conduit support 320 is positioned in the conduit 202 and implanted at the same time the conduit 202 is implanted, and in one embodiment, conduit support 320 is integral to vascular conduit 202. In one embodiment, conduit support 320 comprises a filament structure interwoven with vascular conduit 202. While the figures herein show the conduit support as having a plurality of elongated struts that are connected to radial/circular support members or as a tubular braided type structure, other forms are also possible. Examples of other support structures include, but are not limited to, a helical coil and a plurality of interwoven helical coils.

The filaments and braided structures can be any suitable biocompatible material that has the material properties necessary to provide radial support to the conduit. Examples of suitable biocompatible metallic materials include, but are not limited to nitinol, stainless steel, a cobalt-based alloy, and a nickel cobalt super alloy. Examples of suitable biocompatible polymeric materials include, but are not limited to, include amides, polyimides, polyolefins, polyesters, urethanes, thermoplastics, thermoset plastics, and blends, laminates or copolymers thereof. In one embodiment, conduit support 320 is a braided structure composed of nitinol filaments that are interwoven with the vascular conduit 202. Examples of other suitable biocompatible materials include, but are not limited to, glass fibers and ceramic fibers.

The support structures may also include materials having a high X-ray attenuation coefficient (radiopaque materials) so that the conduit can be easily located and identified. Examples of suitable materials include, but are not limited to, barium sulfate and bismuth sub-carbonate for plastics, and gold and platinum for metals. In one embodiment of the invention, the conduit includes a metal support structure having a gold plating on some portions thereof.

In one embodiment, the braided structure 322 includes nitinol strands of the conduit support 320 intertwined with the material strands of the vascular conduit 202. In one embodiment, the vascular conduit is composed of a woven material made of polyester fibers. In one example, the braiding comprises interweaving three or more separate strands of two or more materials of the conduit support 320 and vascular conduit 202 in a diagonally overlapping pattern.

Figure 5:
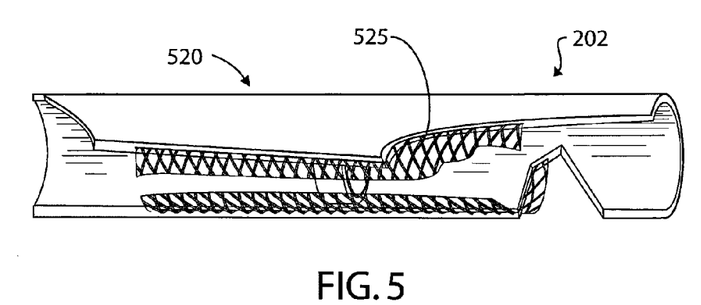
FIG. 5 is a schematic view of one embodiment of a vascular conduit with a conduit support, in accordance with the present invention.

In another embodiment, conduit support 520 comprises a plurality of filaments 525 threaded through and around the walls of a bovine bioprosthetic conduit. In one embodiment, illustrated in FIG. 5, only a portion of the bioprosthetic conduit includes the threaded filaments. In an example, the threaded filaments 525 that comprise the conduit support 520 are located in a middle portion of the conduit 202. Those with skill in the art will recognize that the conduit support may encompass the entire conduit or only a portion of the conduit depending on the specific application.

Figure 6:
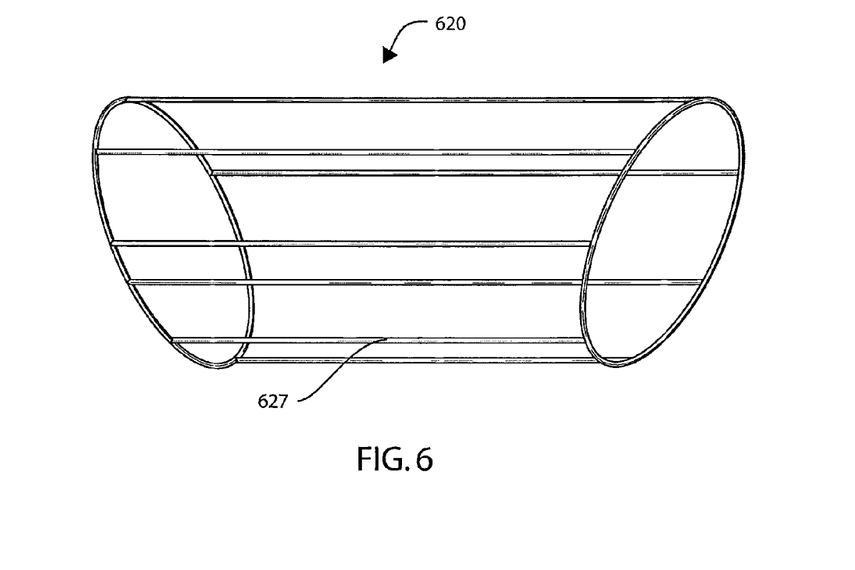
FIG. 6 is a schematic view of another embodiment of a conduit support, in accordance with the present invention.
Figure 7:
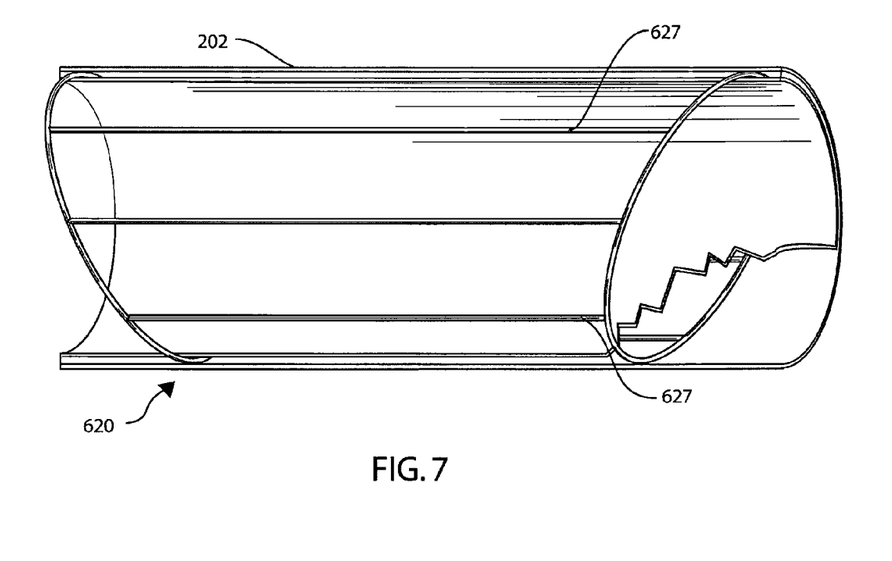
FIG. 7 is a schematic view of the conduit support illustrated in FIG. 4C positioned within a vascular conduit, in accordance with the present invention.

In another embodiment, shown in FIG. 6, conduit support 620 comprises a tubular structure composed of a framework of interconnected support members 627. Both ends of the conduit support are angled for insertion into a conduit having two angled ends (similar to the conduit having one angled end shown in FIG. 2C). The framework of support members includes a substantially circular cross-section. In this embodiment, conduit support 620 is positioned within a lumen of a vascular conduit prior to the implantation of the conduit. Once implanted, the framework of support members provides a substantially circular cross-section to the vascular conduit. Conduit support 620 may be attached to the vascular conduit by, for example, suturing, adhesive, or a combination thereof. In this embodiment, the inner surface of the vascular conduit contacts the outer surface of the support members 627. Conduit support 620 is composed of rigid biocompatible metallic or polymeric material. In another embodiment, illustrated in FIG. 7, conduit support 620 is integral with the conduit 202, positioned within the conduit wall.

Figure 8:
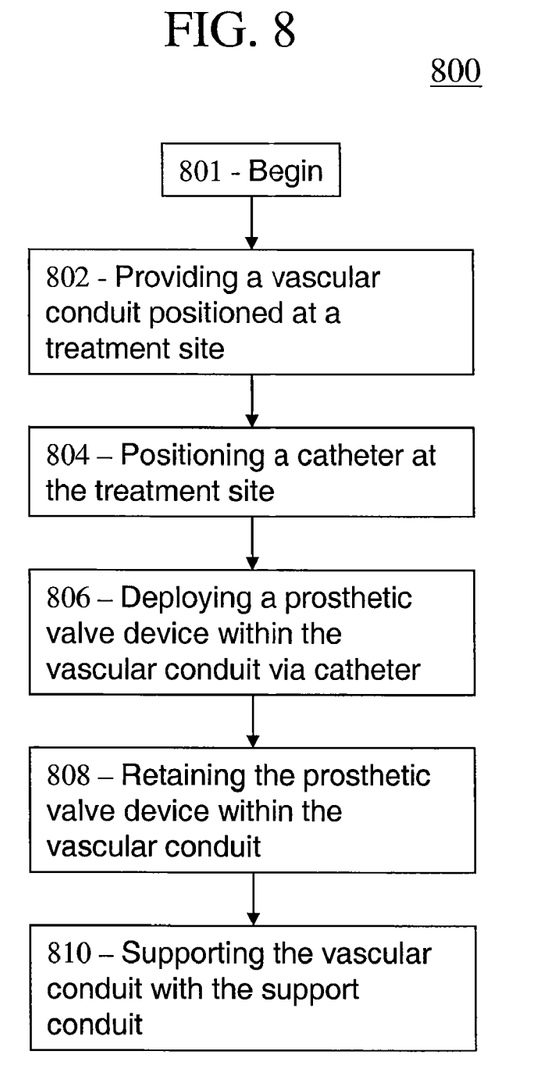
FIG. 8 is a flowchart illustrating a method for treating right ventricular outflow tract abnormalities by replacing a pulmonary valve, in accordance with the present invention.

FIG. 8 is a flowchart illustrating method 800 for treating right ventricular outflow tract abnormalities by replacing a pulmonary valve, in accordance with the present invention. Method 800 begins at 801. Vascular conduit 202 is positioned at a treatment site and includes a conduit support 320 that is integral to or positioned within the vascular conduit 202, as indicated at Block 802. In one embodiment, the conduit support comprises a plurality of nitinol filaments interwoven with the vascular conduit. In one embodiment, conduit support 320 is braided into vascular conduit 202. In another embodiment, conduit support is positioned with the lumen of the vascular conduit and secured to the inner wall of the vascular conduit 206. The vascular conduit 202 is supported in the radial direction by conduit support 320.

Distal portion of catheter 310 is inserted into the vascular system of the patient, advanced to the right ventricular outflow tract and positioned at the treatment site within vascular conduit 202, as indicated at Block 804. Next, prosthetic valve device 300 is deployed from catheter 310, as indicated at Block 806.

At Block 810, the prosthetic valve device 300 is retained within vascular conduit 202. Prosthetic valve device 300 can be retained by the expansive nature of a shape memory stent that forms the support structure 302 of the prosthetic valve device 300.

As indicated in Block 810, the vascular conduit 202 is supported by the nitinol conduit support 320.

While the embodiments of the invention disclosed herein are presently considered preferred, various changes and modifications can be made without departing from the spirit and scope of the invention. For example, the vascular conduit, prosthetic valve device, valve, support structure, conduit support, and catheter are not limited to the illustrated and described embodiments. In addition, the method disclosed for replacing a pulmonary valve may vary.

The current invention discloses surgically implantable, valved conduits that are configured to ease the subsequent implantation of percutaneous catheter based placement of stented valves. In a preferred embodiment, the valves are attached to an expandable structure and they are placed in the valved conduit. The expandable structure can be expanded such that any pre-existing valve in the conduit is not disturbed, or it can be expanded such that any pre-existing valve is pinned between the structure and the interior wall of the conduit.

The delivery catheter carrying the stented valve is passed through the venous system and into a patient's right ventricle. This may be accomplished by inserting the delivery catheter into either the jugular vein or the subclavian vein and passing it through superior vena cava into right atrium. The catheter is then passed through the tricuspid valve, into right ventricle, and out of the ventricle into the conduit. Alternatively, the catheter may be inserted into the femoral vein and passed through the common iliac vein and the inferior vena cava into the right atrium, then through the tricuspid valve, into the right ventricle and out into the conduit. The catheters used for the procedures described herein may include radiopaque markers as is known in the art, and procedure may be visualized using fluoroscopy, echocardiography, ultrasound, or other suitable means of visualization.

Upon reading the specification and reviewing the drawings hereof, it will become immediately obvious to those skilled in the art that myriad other embodiments of the present invention are possible, and that such embodiments are contemplated and fall within the scope of the presently claimed invention. The scope of the invention is indicated in the appended claims, and all changes that come within the meaning and range of equivalents are intended to be embraced therein.

What is claimed is:

1. A vascular valve replacement system, the system comprising:
   a vascular conduit having a long axis and a lumen communicating therethrough;
   a conduit support operably connected to the vascular conduit to reinforce the vascular conduit along the length of the vascular conduit;
   the conduit support comprising a substantially circular cross-section and wherein the conduit support comprises a braided structure interwoven with the vascular conduit, and wherein the vascular conduit comprises a woven polyester fabric; and
   a prosthetic valve device including a valve operably connected to a support structure, the prosthetic valve device positioned within the vascular conduit adjacent to the conduit support.

2. The system of claim 1 wherein the prosthetic valve device is deployed within the lumen of the vascular conduit with a delivery catheter.

3. The system of claim 1 wherein the conduit support provides reinforcement to the vascular conduit in a radial direction.

4. The system of claim 1 wherein the support structure comprises an expandable stent for retaining the prosthetic valve device within the vascular conduit.

5. A pulmonary valve replacement system comprising:
a delivery catheter;
an inflatable member operably attached to the catheter;
a vascular conduit having a long axis and a lumen communicating therethrough;
a conduit support operably connected to the vascular conduit to reinforce the vascular conduit along the length of the vascular conduit;
the conduit support comprising a substantially circular cross-section and wherein the conduit support comprises a braided structure interwoven with the vascular conduit, and wherein the vascular conduit comprises a woven polyester fabric; and
a prosthetic valve device including a valve operably connected to a support structure, the prosthetic valve device disposed on the inflatable member for delivery to the vascular conduit.

6. The system of claim 5 wherein the conduit support provides reinforcement to the vascular conduit in a radial direction.

7. The system of claim 5 wherein the support structure comprises an expandable stent for retaining the prosthetic valve device within the vascular conduit.

8. A method for replacing a pulmonary valve, the method comprising:
providing a vascular conduit positioned at a treatment site, the vascular conduit having a long axis and a lumen communicating therethrough and the vascular conduit further including a conduit support positioned within the vascular conduit wherein the conduit support comprises a braid structure interwoven with the vascular conduit;
supporting the vascular conduit with the conduit support; and
deploying a prosthetic valve device within the vascular conduit via a delivery catheter, the prosthetic valve device including a valve operably connected to a support structure.

9. The method of claim 8 wherein the conduit support comprises nitinol.

10. The method of claim 8 wherein supporting the vascular conduit comprises reinforcing the vascular conduit in a radial direction.

11. The method of claim 8 further comprising retaining the prosthetic valve device within the vascular conduit.

* * * * *